United States Patent
Taylor et al.

(10) Patent No.: US 10,162,939 B2
(45) Date of Patent: Dec. 25, 2018

(54) SYSTEMS AND METHODS FOR IDENTIFYING AND MODELING UNRESOLVED VESSELS IN IMAGE-BASED PATIENT-SPECIFIC HEMODYNAMIC MODELS

(71) Applicant: HeartFlow, Inc., Redwood City, CA (US)

(72) Inventors: Charles A. Taylor, Atherton, CA (US); Hyun Jin Kim, San Mateo, CA (US); Leo Grady, Millbrae, CA (US); Rhea Tombropoulos, Woodside, CA (US); Gilwoo Choi, Mountain View, CA (US); Nan Xiao, Redwood City, CA (US); Buzzy Spain, San Mateo, CA (US)

(73) Assignee: HeartFlow, Inc., Redwood City, CA (US)

( * ) Notice: Subject to any disclaimer, the term of this patent is extended or adjusted under 35 U.S.C. 154(b) by 2 days.

(21) Appl. No.: 15/442,102

(22) Filed: Feb. 24, 2017

(65) Prior Publication Data

US 2017/0249439 A1 Aug. 31, 2017

Related U.S. Application Data

(60) Provisional application No. 62/300,540, filed on Feb. 26, 2016.

(51) Int. Cl.
 *G06F 19/00* (2018.01)
 *G16H 50/50* (2018.01)
(52) U.S. Cl.
 CPC .......... *G06F 19/3437* (2013.01); *G06F 19/00* (2013.01); *G16H 50/50* (2018.01)

(58) Field of Classification Search
 CPC .......................... G06F 19/3437; G16H 50/50
 See application file for complete search history.

(56) References Cited

U.S. PATENT DOCUMENTS

| 8,315,812 | B2 | 11/2012 | Taylor | |
|---|---|---|---|---|
| 2010/0266172 | A1* | 10/2010 | Shlomi | G09B 23/285 |
| | | | | 382/128 |

FOREIGN PATENT DOCUMENTS

| WO | WO 2013/071219 | 5/2013 |
|---|---|---|
| WO | WO 2015/148401 | 10/2015 |
| WO | WO 2015/164086 | 10/2015 |

OTHER PUBLICATIONS

Spilker, Ryan L. et al., "Morphometry-Based Impedance Boundary Conditions for Patient-Specific Modeling of Blood Flow in Pulmonary Arteries", Annals of Biomedical Engineering, Kluwer Academic Pubilshers-Plenum Publishers, NE, vol. 35, No. 4, Feb. 9, 2007, pp. 546-559.

(Continued)

*Primary Examiner* — Nicholas Tobergte
(74) *Attorney, Agent, or Firm* — Bookoff McAndrews, PLLC

(57) ABSTRACT

Systems and methods are disclosed for identifying and modeling unresolved vessels, and the effects thereof, in image-based patient-specific hemodynamic models. One method includes: receiving, in an electronic storage medium, one or more patient-specific anatomical models representing at least a vessel of a patient; determining, using a processor, the values and characteristics of one or more patient-specific morphometric features in the one or more patient-specific anatomical models; modifying the patient-specific anatomical model using the determined patient-specific morphometric features; and outputting, one or more (Continued)

of, a modified patient-specific anatomical model or a patient-specific morphometric feature to an electronic storage medium or display.

20 Claims, 8 Drawing Sheets

(56) References Cited

OTHER PUBLICATIONS

International Search Report issued in related PCT/US2017/019462 dated Jul. 4, 2017 (17 pgs).
Kassab, G. S., C. A. Rider, N. J. Tang, and Y. C. Fung. Morphometry of pig coronary arterial trees. Am. J. Physiol. 265:H350-365, 1993.
Kassab, G. S., J. Berkley, and Y. C. Fung. Analysis of pig's coronary arterial blood flow with detailed anatomical data. Ann. Biomed. Eng. 25:204-217, 1997.
Huo Y, Wischgoll T, Choy JS, Sola S, Navia JL, Teague SD, et al. CT-based diagnosis of diffuse coronary artery disease on the basis of scaling power laws. Radiology 2013;268:694-701.
M. Anliker, L. Rockwell, and E. Ogden, "Nonlinear Analysis of Flow Pulses and Shock Waves in Arteries," ZAMP, vol. 22, pp. 217-246, 1971.
Hughes, T. J. R. and J. Lubliner. On the one-dimensional theory of blood flow in the larger vessels. Math. Biosci. 18:161-170, 1973.

\* cited by examiner

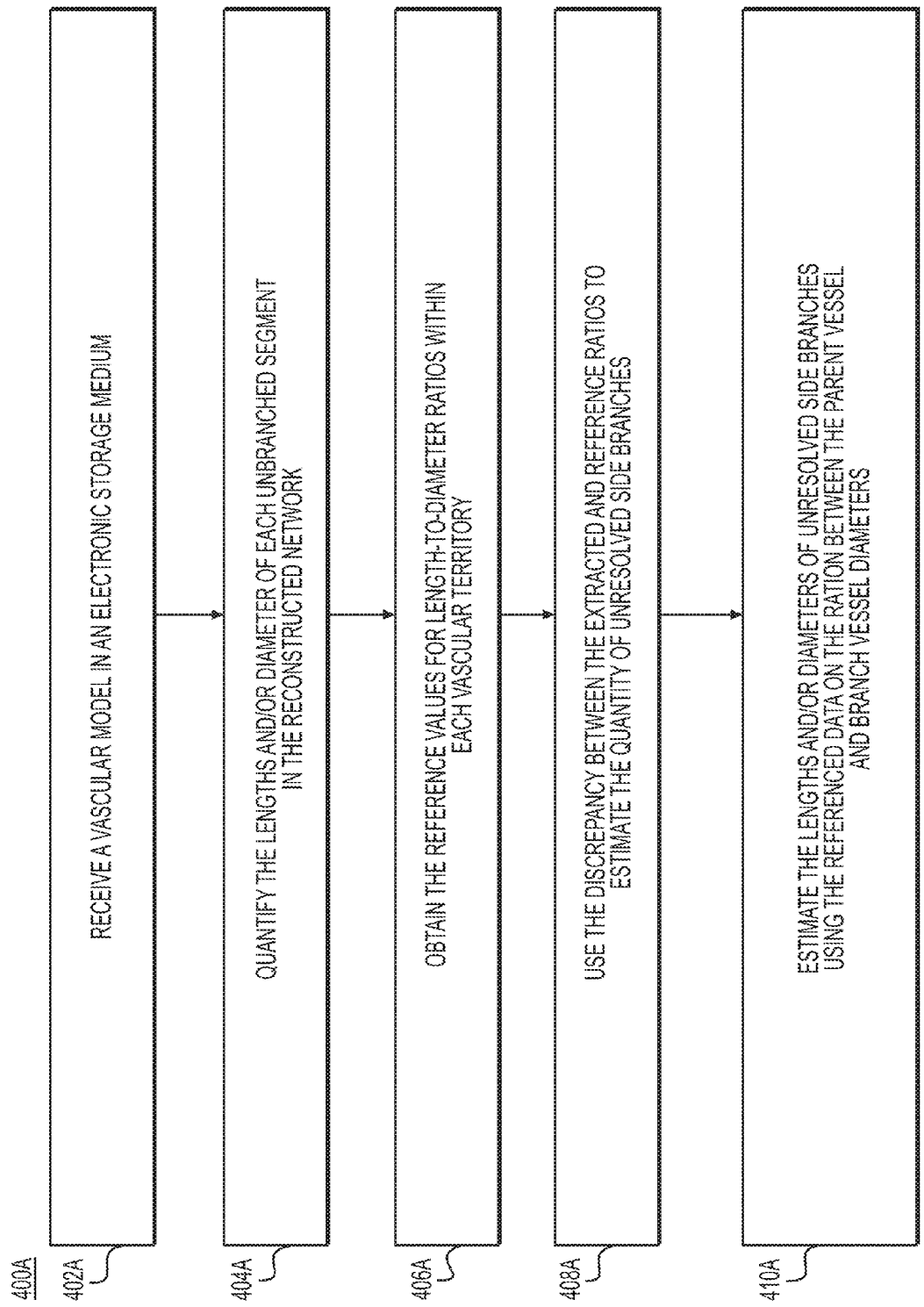

SYSTEMS AND METHODS FOR IDENTIFYING AND MODELING UNRESOLVED VESSELS IN IMAGE-BASED PATIENT-SPECIFIC HEMODYNAMIC MODELS

RELATED APPLICATION(S)

This application claims priority to U.S. Provisional Application No. 62/300,540 filed Feb. 26, 2016, the entire disclosure of which is hereby incorporated herein by reference in its entirety.

FIELD OF THE DISCLOSURE

Various embodiments of the present disclosure relate generally to medical imaging, image matching, and related methods. More specifically, particular embodiments of the present disclosure relate to systems and methods for identifying and modeling unresolved features and/or the effects thereof.

BACKGROUND

Patient-specific models of blood flow may require an accurate geometric representation of the vascular network of interest. Current medical imaging data may be used to create a three-dimensional anatomic model with blood vessels ranging in size from 10 mm in diameter and above for the large main arteries, 2-5 mm for the large coronary arteries, 1-3 mm for large branch vessels, and less than a millimeter for small branch vessels. Constrained by limited image resolution and quality, these models may directly represent only the portion of the vascular network that may be observable in the image. The vessels that may be resolved may contain side branches that may be just below the limits of the image resolution and which may not be directly extracted from the data. The inclusion and/or exclusion of these branches and their downstream vascular networks may significantly influence the computed hemodynamic quantities in the observable anatomy. For example, in the coronary arterial tree where bifurcations are largely asymmetrical, arteries with cross-sectional dimensions near the limits of image resolution may be likely to give rise to small unseen side branches. Another possible scenario may be that the main vessel paths may be modeled but one or more side branches may not be included due to low image quality, image resolution, operator neglect, or lack of detection or inclusion by one or more automated image processing algorithms. In either case, the reconstructed geometry may contain long, unbranched vessel segments, which may result in artificial pressure gradients even when the vessels are free of disease. Alternatively or additionally, the unresolved vessels may be collateral vessels that may serve to bypass a region of disease and the modeled pressure loss across the diseased region may be larger than in reality due to a failure to include these vessels. Misinterpretation of these phenomena may potentially trigger a misleading diagnosis.

Therefore, there is a desire for a system and method that may 1) estimate the physical locations and geometric configurations of unresolvable and/or un-modeled vascular systems and 2) enhance the accuracy of patient-specific models of blood flow with information on un-modeled vascular systems to mitigate computational artifacts in the directly modeled regions of interest.

SUMMARY

According to certain aspects of the present disclosure, systems and methods are disclosed for identifying and modeling unresolved vessels, and the effects thereof, in image-based patient-specific hemodynamic models.

One method includes: receiving, in an electronic storage medium, one or more patient-specific anatomical models representing at least a vessel of a patient; determining, using a processor, the values and characteristics of one or more patient-specific morphometric features in the one or more patient-specific anatomical models; modifying the patient-specific anatomical model using the determined patient-specific morphometric features; and outputting, one or more of, a modified patient-specific anatomical model or a patient-specific morphometric feature to an electronic storage medium or display.

In accordance with another embodiment, a system for identifying and modeling unresolved vessels, and the effects thereof, in image-based patient-specific hemodynamic models comprises: a data storage device storing instructions for identifying and modeling unresolved vessels, and the effects thereof, in image-based patient-specific hemodynamic models; and a processor configured for: receiving, in an electronic storage medium, one or more patient-specific anatomical models representing at least a vessel of a patient; determining, using a processor, the values and characteristics of one or more patient-specific morphometric features in the one or more patient-specific anatomical models; modifying the patient-specific anatomical model using the determined patient-specific morphometric features; and outputting, one or more of, a modified patient-specific anatomical model or a patient-specific morphometric feature to an electronic storage medium or display.

In accordance with another embodiment, a non-transitory computer readable medium for use on a computer system containing computer-executable programming instructions for performing a method of identifying and modeling unresolved vessels, and the effects thereof, in image-based patient-specific hemodynamic models, the method comprising: receiving, in an electronic storage medium, one or more patient-specific anatomical models representing at least a vessel of a patient; determining, using a processor, the values and characteristics of one or more patient-specific morphometric features in the one or more patient-specific anatomical models; modifying the patient-specific anatomical model using the determined patient-specific morphometric features; and outputting, one or more of, a modified patient-specific anatomical model or a patient-specific morphometric feature to an electronic storage medium or display.

Additional objects and advantages of the disclosed embodiments will be set forth in part in the description that follows, and in part will be apparent from the description, or may be learned by practice of the disclosed embodiments. The objects and advantages of the disclosed embodiments will be realized and attained by means of the elements and combinations particularly pointed out in the appended claims.

It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which are incorporated in and constitute a part of this specification, illustrate various exemplary embodiments, and together with the description, serve to explain the principles of the disclosed embodiments.

FIGS. 4A-4D are block diagrams of exemplary methods for determining the values and characteristics of unresolved and/or unmodeled segments of a vascular model, according to an exemplary embodiment of the present disclosure.

The steps described in the methods may be performed in any order, or in conjunction with any other step. It is also contemplated that one or more of the steps may be omitted for performing the methods described in the present disclosure.

DESCRIPTION OF THE EMBODIMENTS

Reference will now be made in detail to the exemplary embodiments of the disclosure, examples of which are illustrated in the accompanying drawings. Wherever possible, the same reference numbers will be used throughout the drawings to refer to the same or like parts.

Various embodiments of the present disclosure may provide systems and methods for estimating the physical locations, geometric configurations (e.g., cross-sectional diameter), and/or effects of unresolvable and/or un-modeled vascular systems and enhancing the accuracy of patient-specific models of blood flow with information on un-modeled vascular systems to mitigate computational artifacts in the directly modeled regions of interest.

Figure 2:
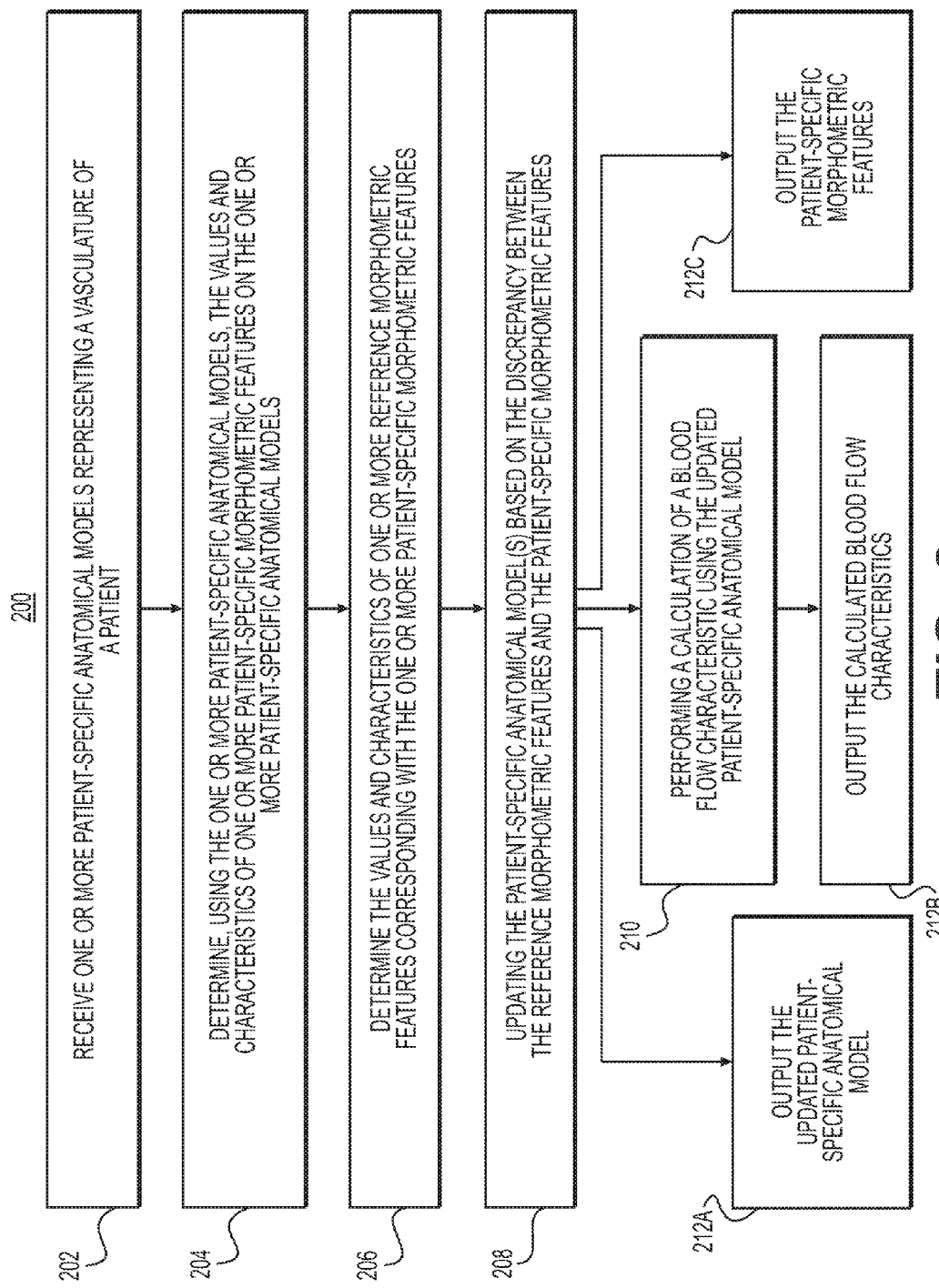
FIG. 2 is a block diagram of a general method of identifying and modeling unresolved vessels, and the effects thereof, in image-based patient-specific hemodynamic models, according to an exemplary embodiment of the present disclosure.

According to a general embodiment of the present disclosure, as depicted in FIG. 2, one method may include receiving one or more patient-specific anatomical models of a patient from an electronic storage device, determining the values and characteristics of one or more patient-specific morphometric features on the one or more patient-specific anatomical models, determining the values and characteristics of one or more reference morphometric features corresponding with the one or more patient-specific morphometric features, updating the original patient-specific anatomical models based on the discrepancy between the reference morphometric features and the patient-specific morphometric features, performing a calculation of a blood flow characteristic using the updated patient-specific model, and outputting one or more of the calculated blood flow characteristics, updated patient-specific anatomical model, or patient-specific morphometric features.

Furthermore, various embodiments of the present disclosure also apply the systems and methods discussed above to particular vascular regions (e.g., the coronary vascular region and the myocardium), or to obtaining and/or using specific information on unmodeled vascular systems (e.g., un-modeled side branches) to enhance the accuracy of patient-specific models of blood flow. For example, the myocardium may be divided into six distinct zones; "distributing vessels" may run along the zone borders and "delivering vessels" may branch off the distributing vessels and penetrate into the myocardial tissue zones. The coronary vasculature may have bifurcations that may be predominantly asymmetric. For example, a parent trunk (e.g., distributing vessel) may branch out to two daughter vessels (e.g., delivering vessels), where one of the daughter vessels may be much closer in diameter to the parent trunk. That is, each daughter vessel may have a differing geometric configuration. If the parent trunk (e.g. a distributing vessel) is large enough to be resolved by medical imaging, but a daughter vessel (e.g., delivering vessel) is below the limits of image resolution, the resulting reconstruction of the coronary arterial network may contain long unbranched segments. Stated differently, the resulting reconstruction may exclude the unresolved daughter vessel that is below the limits of image resolution. A simulation of blood flow based on such a partial reconstruction may result in large pressure gradients in the distal regions. Higher flow rates may be predicted in the vessel segments with un-modeled branches than would occur naturally, potentially leading to physiologically unrealistic pressure losses.

Modeling the unobserved vessel branches may include trimming patient-specific anatomic models based on anatomic landmarks and ad hoc size criteria. Exemplary trimming rules may include size-based criteria. Alternately or in addition, the modeling may include generating branch vessels using branching rules and/or accounting for missed branches using a vessel wall permeability function (e.g., as in method 500B). In one embodiment, an algorithm assessing cross-sectional area changes along the length of vessels may include modeling branch vessels. One embodiment for modeling the effect of unobserved coronary branches by addition of side branches may be depicted FIG. 3, according to an exemplary embodiment of the current disclosure.

Figure 1:
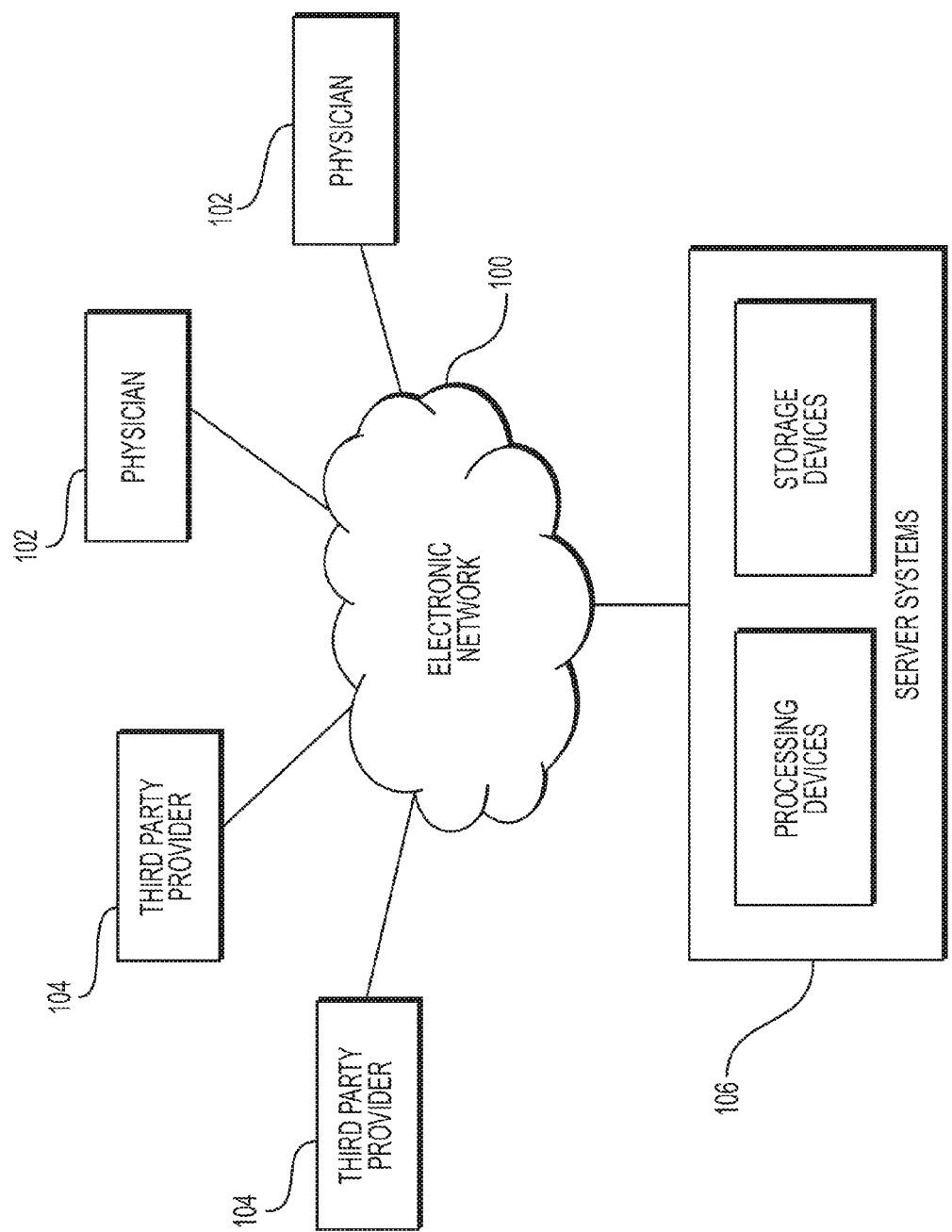
FIG. 1 is a block diagram of an exemplary system and network for identifying and modeling unresolved vessels, and the effects thereof, in image-based patient-specific hemodynamic models, according to an exemplary embodiment of the present disclosure.

Referring now to the figures, FIG. 1 depicts a block diagram of an exemplary system 100 and network for identifying and modeling unresolved vessels, and the effects thereof, in image-based patient-specific hemodynamic models, according to an exemplary embodiment. Specifically, FIG. 1 depicts a plurality of physicians 102 and third party providers 104, any of whom may be connected to an electronic network 100, such as the Internet, through one or more computers, servers, and/or handheld mobile devices. Physicians 102 and/or third party providers 104 may create or otherwise obtain images of one or more patients' anatomy. The physicians 102 and/or third party providers 104 may also obtain any combination of patient-specific and/or reference morphometric features, including, but not limited to, measurements of vessel cross-sectional areas, the rate of change of a vessel cross-sectional area along the vessel, length-to-diameter ratios, volumes, connectivity patterns, Strahler numbers, the identity of local vascular territory, etc.

Physicians 102 and/or third party providers 104 may transmit the anatomical images and/or information on morphometric features to server systems 106 over the electronic network 100. Server systems 106 may include storage devices for storing images and data received from physicians 102 and/or third party providers 104. Server systems 106 may also include processing devices for processing images and data stored in the storage devices.

Figure 3:
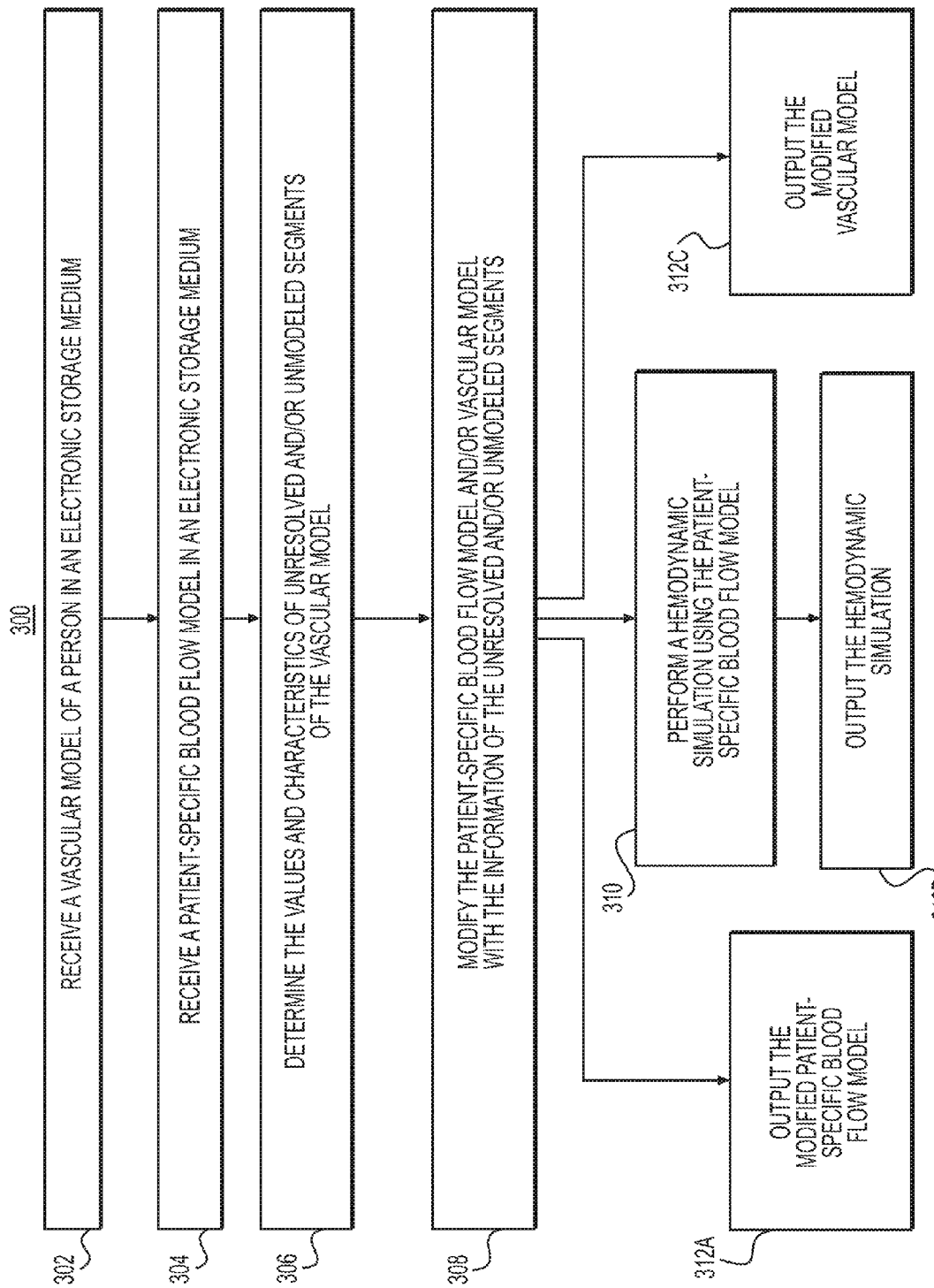
FIG. 3 is a block diagram of an exemplary method of identifying and modeling unresolved vessels, and the effects thereof, in image-based patient-specific hemodynamic models, where the unresolved vessels may be unobserved coronary branches, and where the modeling the effects of unobserved coronary branches may include the addition of side branches, according to an exemplary embodiment of the present disclosure.

FIG. 2 depicts a general embodiment of a method 200 for identifying and modeling unresolved vessels, and the effects thereof, in image-based patient-specific hemodynamic models. FIG. 3 depicts an exemplary embodiment of the method of FIG. 2, where the unresolved vessels may be unobserved coronary branches, and where the modeling the effects of unobserved coronary branches may include the addition of side branches. FIGS. 4A-4D depict various methods (e.g., 400A-400D) for determining the values and characteristics of unresolved and/or unmodeled segments of a vascular model, which may be a step performed in methods 200 and 300 of FIGS. 2 and 3, respectively. FIG. 5 depicts method 500 of modifying a vascular and/or blood flow model with information on unresolved and/or unmodeled segments, which may be a step performed in methods 200 and 300 of FIGS. 2 and 3, respectively.

FIG. 2 is a block diagram of a method 200 of identifying and modeling unresolved vessels, and the effects thereof, in image-based patient-specific hemodynamic models, according to a general embodiment. The method of FIG. 2 may be performed by server systems 106, based on information, images, and data received from physicians 102 and/or third party providers 104 over electronic network 101.

In one embodiment, step 202 may include receiving one or more patient-specific anatomical models representing a vasculature of a patient. The one or more patient-specific anatomical models may be received from an electronic storage device (e.g., a hard drive, network drive, etc.) and/or may be saved upon receipt to an electronic storage device. In some embodiments, the one or more models may represent the vasculature of a patient in one or more physiological states (e.g., normal, rest, exercise-induced hyperemia, drug-induced hyperemia, etc.) and/or temporal states (e.g., future, past, prospective, etc.). In some embodiments, the patient-specific anatomical models may be received using a computational device (e.g., a computer, laptop, digital signal processing device, smart phone, etc.). In an alternate embodiment, the model may be reconstructed from image data of a vascular anatomy, without including the side branches of main vessels. For example, a coronary blood flow model may contain the three main coronary vessels without side branches. These branches may have been impossible to resolve in a medical image due to noise or imaging artifacts. In such an embodiment, the side branches emanating from a parent vessel may be estimated and modeled as described in the embodiments of the present disclosure (e.g., as in steps 204 to 210).

Step 204 may include determining, using the one or more patient-specific anatomical models, the values and characteristics of one or more patient-specific morphometric features on the one or more patient-specific anatomical models. In one embodiment, the one or more morphometric features may be determined from patient-specific anatomical models representing different phases of a cardiac cycle. The one or more morphometric features may include, but are not limited to, measurements of vessel cross-sectional areas, the rate of change of a vessel cross-sectional area along the vessel, length-to-diameter ratios, volumes, connectivity patterns, Strahler numbers, the identity of local vascular territory, etc.

Step 206 may include determining the values and characteristics of one or more reference morphometric features corresponding with the one or more patient-specific morphometric features. In one embodiment, the one or more reference morphometric features may be measured, derived, or obtained from image data, data from the literature, computed patient or population databases, and/or from a learned relationship.

Step 208 may include updating the original patient-specific anatomical models based on the discrepancy between the reference morphometric features and the patient-specific morphometric features. The method may include the addition of branches to vessel segments or modeling the presence of additional branches, e.g., via permeability of the vessel walls in the directly observable regions.

In some embodiments, the discrepancy between the reference and extracted morphometric information may instead be used to define the extent of the patient-specific computational domain such that the maximal patient-specific anatomy may be included in the patient-specific anatomical models without introducing physiologically implausible predictions in the main arteries of interest. The computational domain of the patient-specific anatomical models may then be artificially truncated to exclude regions that are most likely to contain unresolved vessel systems. In such embodiments, step 208 may include identifying the additional branches as a result of the discrepancy between the reference and extracted morphometric information, but instead of augmenting the model with the additional branches, the model may be truncated. For example, the patient-specific anatomic model may be truncated after the actual effective cross-sectional area falls below a predetermined threshold, e.g., 90% of the expected cross-sectional area.

Step 210 may include performing a calculation of a blood flow characteristic using the updated patient-specific model. In some embodiments, a blood flow characteristic may include, but is not limited to, a fractional flow reserve (FFR) value, a blood flow magnitude or direction, a perfusion characteristic, a pressure value, a blood flow velocity, or a combination thereof.

Steps 212A-C may include outputting, one or more of, the updated patient-specific anatomical model (e.g., step 212A), the calculated blood flow characteristic (e.g., step 212B), or patient-specific morphometric features (e.g., step 212C). In some embodiments, one output or set of outputs (e.g., the calculated blood flow characteristic and/or the patient-specific morphometric features) may be overlaid or displayed on another output or set of outputs (e.g., the updated patient-specific anatomical model). In one embodiment, the output may be provided to a user through a report and/or through a computer output device, e.g., as an electronic storage medium.

FIG. 3 is a block diagram of a method 300 of identifying and modeling unresolved vessels, and the effects thereof, in image-based patient-specific hemodynamic models, according to an exemplary embodiment, where the unresolved vessels may be, e.g., unobserved coronary branches (or other blood vessels), and where the modeling the effects of unobserved coronary branches may include the addition of side branches. The method of FIG. 3 may be performed by server systems 106, based on information, images, and data received from physicians 102 and/or third party providers 104 over electronic network 101. Moreover, FIG. 3 may provide a method of modeling the effect of unobserved coronary branches by addition of side branches.

In one embodiment, step 302 may include receiving a vascular model of a person. The vascular model may be of any suitable blood vessels, e.g., coronary blood vessels. For exemplary purposes only, the following description is provided for coronary vessels. The coronary patient-specific anatomical models may be received from an electronic storage device (e.g., a hard drive, network drive, etc.). Alternatively or additionally, the one or more patient-specific anatomical models may be received in an electronic storage device. The model may represent the patient in one or more physiological states (e.g., normal, rest, exercise-induced hyperemia, drug-induced hyperemia, etc.) and/or temporal states (e.g., future, past, prospective, etc.). The patient-specific anatomical models may be received using a computational device (e.g., a computer, laptop, DSP, smart phone, etc.). In one embodiment, a coronary vessel model may be a 3D surface mesh model and/or a 1D network of vessels. In another embodiment, the coronary vessel model may be obtained from segmentation of a medical imaging data using one or more scanning modalities (e.g., computed tomography, magnetic resonance, ultrasound, etc.). In yet another embodiment, the patient-specific coronary model may be received using a computational device (e.g., a computer, laptop, DSP, smart phone, etc.).

Step 304 may include receiving a patient-specific blood flow model in an electronic storage device. In some embodiments, the blood flow model is obtained, calculated, or derived from the received coronary vascular model. Step 304 may be performed by a processor of server systems 106.

Step 306 may include determining the values and characteristics of unresolved and/or unmodeled segments of the coronary vascular model and/or blood flow model. In some embodiments, step 306 may include estimating the presence of un-modeled branches of the coronary vascular model. Step 306 may be performed using a variety of methods, including, but not limited to, a method involving the length-to-diameter ratio (e.g., as in method 400A depicted in FIG. 4A), a method involving a synthesized downstream vascular tree (e.g., as in method 400B depicted in FIG. 4B), a method involving the cross-sectional area of a vessel (e.g., as in method 400C depicted in FIG. 4C), and a method using a machine learning algorithm (e.g., as in method 400D depicted in FIG. 4D). Step 306 may be performed by a processor of server system 106. In some embodiments, step 306 may include storing the values and characteristics of the unresolved and/or unmodeled segments in an electronic storage device.

Step 308 may include modifying the blood flow model and/or vascular model with the information of the unresolved branches and/or unmodeled segments. Step 308 may be performed by a selection of one or more methods, including but not limited to, augmenting a blood flow model and/or vascular anatomical model with additional branches (e.g., as in method 500A depicted in FIG. 5), or defining a permeability function whereby blood flow may be extracted along the length of a vessel in order to reduce the pressure gradient (e.g., as in method 500B depicted in FIG. 5). In some embodiments, step 308 may include readjusting the boundary conditions of the blood flow model and/or coronary vascular model. Step 308 may be performed by a processor of server systems 106.

In some embodiments, where modifying the blood flow model and/or coronary vascular model includes the identification of additional branches, step 308 may include artificially truncating the computational domain of the patient-specific blood flow model and/or coronary vascular model to exclude regions that are most likely to contain unresolved vessel systems. In such embodiments, step 308 may include, instead of augmenting the model with additional branches using the values and characteristics of unresolved and/or unmodeled segments of the coronary vascular model, truncating the model to exclude the unresolved and/or unmodeled vascular segments and/or vessel systems.

Step 310 may include performing a hemodynamic simulation using a modified blood flow model and/or coronary vascular anatomical model. Blood flow simulations may be performed by any numerical method typically used for solving three-dimensional, one-dimensional, lumped-parameter, and/or physics-based models. In some embodiments, a hemodynamic simulation may include a computation over a time period (e.g., a duration from 0 to N) of properties pertaining to blood flow or its impact on organ systems. Examples of these properties may include, but are not limited to, pressure, flow velocity, transmission of a contrast agent or drug, coronary wall stress, organ perfusion, or values derived from these properties, e.g., fractional flow reserve or coronary flow reserve. Alternatively or additionally, machine learning based methods may be used to perform a hemodynamic simulation or obtain values of one or more hemodynamic properties.

Steps 312A-D may include outputting one or more of the modified patient-specific blood flow model (e.g., as in step 312A), the hemodynamic simulation (e.g., as in step 312B) or the modified coronary vascular model (e.g., as in step 312C). In one embodiment, steps 312A-D may also include outputting the determined values and characteristics of unresolved and/or unmodeled segments of the blood flow model and/or coronary vascular model. In some embodiments, one output or set of outputs (e.g., the hemodynamic simulation and/or values and characteristics of the unresolved and/or unmodeled segments of the original model) may be overlaid or displayed on another output or set of outputs (e.g., the modified blood flow model and/or modified coronary vascular model). In one embodiment, the output may be provided to a user through a report and/or through a computer output device, e.g., as an electronic storage medium.

FIGS. 4A-4D are block diagrams of exemplary methods 400A-400D, respectively, which may determine the values and characteristics of unresolved and/or unmodeled segments of a vascular model, and the effects thereof, according to exemplary embodiments of the present disclosure. Moreover, methods 400A-400D may be used to perform step 206 of method 200 or step 306 of method 300.

For example, FIG. 4A depicts a method 400A of determining the values and characteristics of unresolved and/or unmodeled segments of a vascular model (e.g., a coronary vascular model), using a length-to-diameter ratio method.

Step 402A may include receiving a vascular model in an electronic storage medium (e.g., as in step 302). In some embodiments, the vascular model received may be of a vascular region other than a coronary region. In other embodiments, step 402A, like step 202, may include receiving one or more patient-specific anatomical models representing a vasculature of a patient in one or more physiological or temporal states (e.g., future, past, prospective, etc.).

Step 404A may include quantifying the lengths and diameters of each unbranched and/or unmodeled segment in the reconstructed network. The reconstructed network may be obtained or derived from the vascular network of the received coronary vascular model. In some embodiments, step 404A may include computing a length-to-diameter ratio of one or more unbranched segments of the received coronary vasculature. The length-to-diameter ratio may be computed, e.g., using the average diameter along the segment.

Step 406A may include obtaining reference values for length-to-diameter ratios within each vascular territory. This data may be found from the literature, such as the animal data gathered for the development of the diameter-defined Strahler ordering system described in, e.g., Kassab et al. (Kassab, G. S., C. A. Rider, N. J. Tang, and Y. C. Fung.

Morphometry of pig coronary arterial trees. Am. J. Physiol. 265:H350-365, 1993; Kassab, G. S., J. Berkley, and Y. C. Fung. Analysis of pig's coronary arterial blood flow with detailed anatomical data. Ann. Biomed. Eng. 25:204-217, 1997). Alternatively or additionally, data from conventional coronary angiography (CCA) or intravascular imaging technologies, e.g. optical coherence tomography (OCT), obtained from a population of patients may be used to supplement the estimation of unresolved branches by providing corresponding reference values for the desired length-to-diameter ratios within the vascular territory of interest. These techniques may often enable visualization of small branches beyond the resolution limits of conventional imaging, such as, for example, computed tomography angiography (CTA) image data. An analysis of such data in a population of patients may be used to define a reference morphometric database.

Step 408A may include using the discrepancy between the extracted and reference ratios to estimate the quantity of unresolved side branches. For example, if a morphometric database indicated a branching frequency (e.g., via length-to-diameter ratio) and the ratio of the extracted model was below the reference ratio, it may be desirable in the computation or process introduce additional branches in order to align the extracted with the reference. In another example, vessels without branches with large length-to-diameter ratios may be more likely to have unresolved side branches than segments with lower length-to-diameter ratios.

Step 410A may include estimating the diameters and lengths of unresolved side branches using the reference data on the ratio between parent vessel and branch vessel diameters. In some embodiments, step 410A may include utilizing a statistical analysis and/or machine learning algorithm to determine the diameters and lengths of unresolved side branches.

Figure 4B:
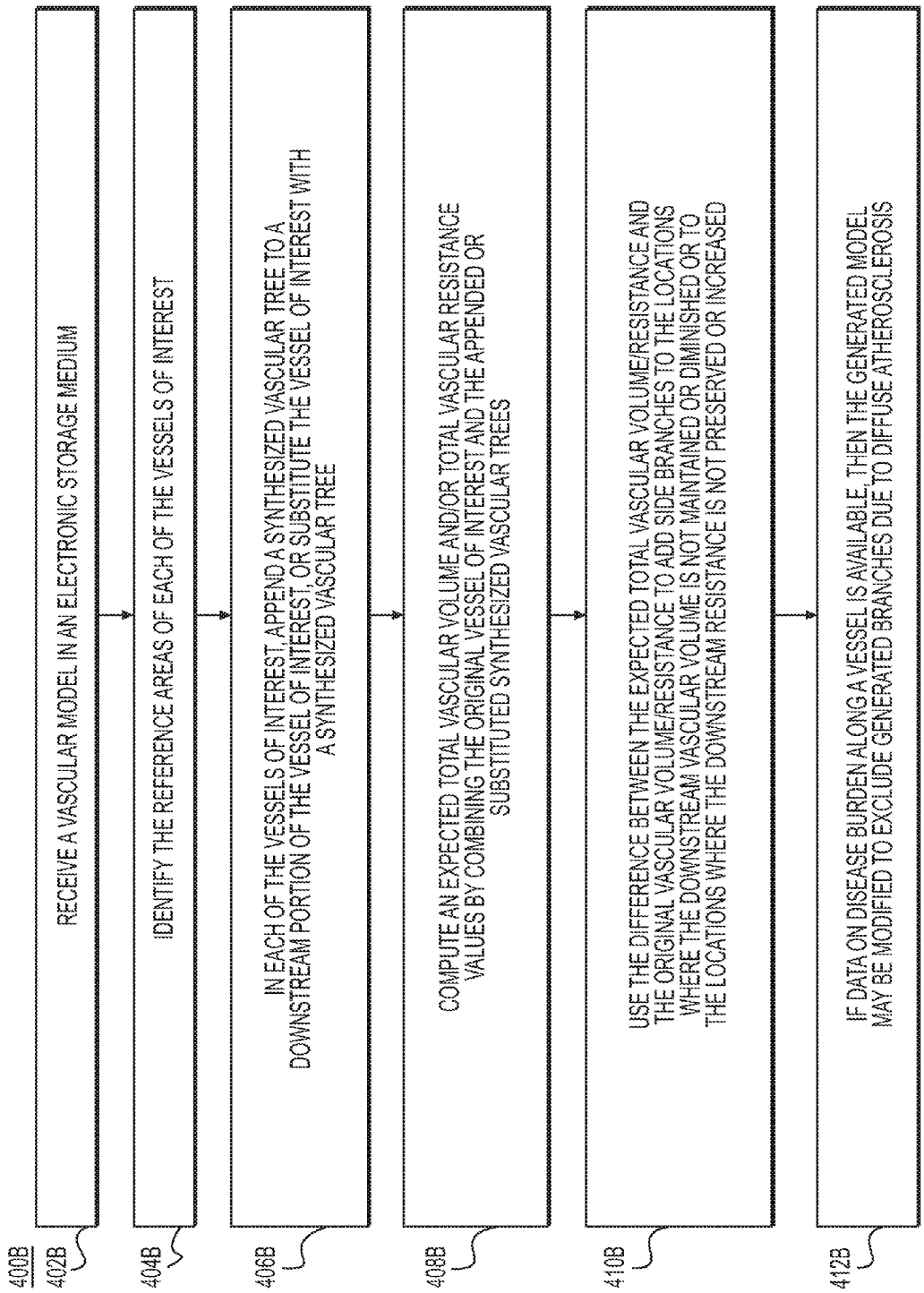
Figure 5:
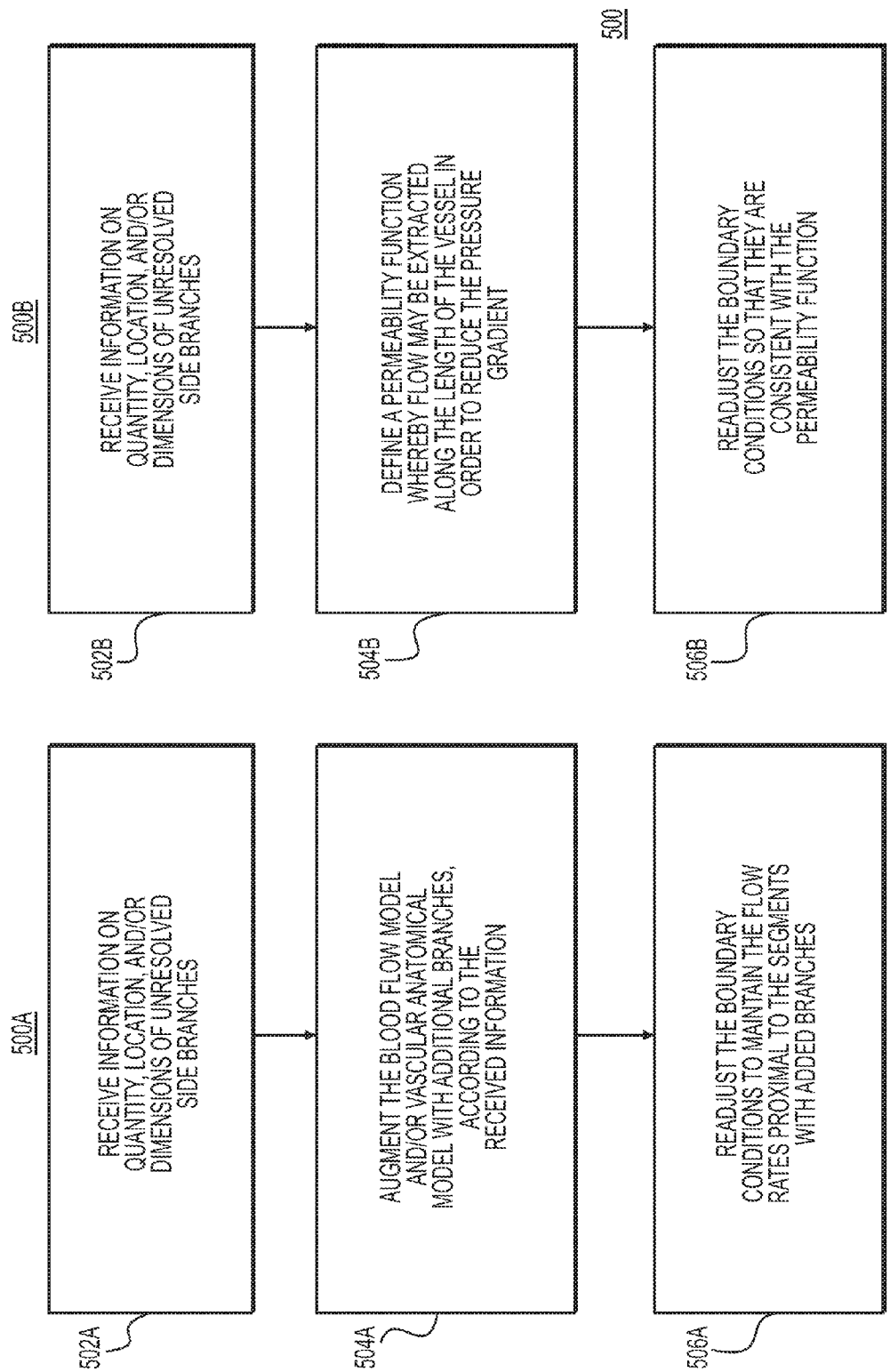
FIG. 5 is a block diagram of an exemplary method for modifying a vascular and/or blood flow model with information on unresolved and/or unmodeled segments, according to an exemplary embodiment of the present disclosure.

FIG. 4B depicts a method 400B of determining the values and characteristics of unresolved and/or unmodeled segments of a vascular model, using one or more of a synthesized downstream vascular tree, total vascular volume, and/or resistance optimization.

Step 402B may include receiving a vascular model (e.g., a coronary vascular model) in an electronic storage medium (e.g., as in step 302). In some embodiments, the vascular model received may be of a vascular region other than a coronary region. In other embodiments, step 402B may include, like step 202, receiving one or more patient-specific anatomical models representing a vasculature of a patient in one or more physiological or temporal states (e.g., future, past, prospective, e.tc.).

Step 404B may include identifying the reference areas of each of the vessels of interest. The reference areas may include, but are not limited to, the cross-sectional area along the length of the vessel segment and/or the diameter of the largest inscribed sphere. Other reference areas may include, for example, smoothed cross-sectional areas (e.g., locally, globally), circumscribed areas, off-tangent areas (e.g., due to smoothing), area and/or eccentricity metrics, etc. In one embodiment, where an optimization and/or regression study may be performed, identifying the reference areas of the vessels of interest may include estimating an ideal and/or healthy diameter for a given vessel segment based on, e.g., the inputs of the cross-sectional area, the largest inscribed sphere diameter, and/or the vessel geometry. Other parameters or methods that may be used to estimate healthy and/or ideal diameters may include, but are not limited to, vessel wall thickness, local or global disease presence, regression of localized or global areas, or any technique that relates patient anatomies to each other via a notion of a transformation distance from one anatomy to the other. Those with ordinary skill in the art will readily recognize that any suitable statistical model may be used to estimate an ideal and/or healthy diameter.

Step 406B may include, in each of the vessels of interest, appending a synthesized vascular tree to a downstream portion of the vessel of interest. Alternatively or additionally, step 406B may include substituting the vessel of interest with a synthesized vascular tree. In one embodiment, the synthesized tree may be described using the diameter-defined Strahler ordering system. The synthesized tree may be designed using morphometry data from literature (e.g., from Kassab, G. S., C. A. Rider, N. J. Tang, and Y. C. Fung. Morphometry of pig coronary arterial trees. Am. J. Physiol. 265:H350-365, 1993), conventional coronary angiography (CCA), or intravascular imaging technologies (e.g. optical coherence tomography (OCT)), obtained in a population of patients. The synthesized tree may extend beyond the resolution limits of CTA image data and may be extended to a fixed diameter value or may be extended down to the pre-capillary level, if needed. The branching patterns of the synthesized tree may be further refined when the locations of the perfused tissues/cells are provided.

Step 408B may include computing an expected total vascular volume or total vascular resistance values. In some embodiments, the computation may include combining the original vessel of interest and the appended or substituted synthesized vascular trees.

Step 410B may include using the difference between the computed expected total vascular volume/resistance and the original vascular volume/resistance to add one or more side branches to the locations where the downstream vascular volume is not maintained or diminished, or to the locations where the downstream resistance is not preserved or increased. Additional side branches may be included if the perfused locations require a denser vascular network.

In some embodiments, if data on disease burden along the vessel is available, e.g., by detecting plaque in the CT data, then step 412B may include modifying the generated model to exclude generated branches due to disease, e.g., diffuse atherosclerosis. This diffuse disease may also be estimated by computing the ratio of the coronary arterial volume to the myocardial mass or volume or the ratio of the arterial lumen volume to the summed length (e.g., as explained in Huo Y, Wischgoll T, Choy J S, Sola S, Navia J L, Teague S D, et al. CT-based diagnosis of diffuse coronary artery disease on the basis of scaling power laws. Radiology 2013; 268:694-701).

Figure 4C:
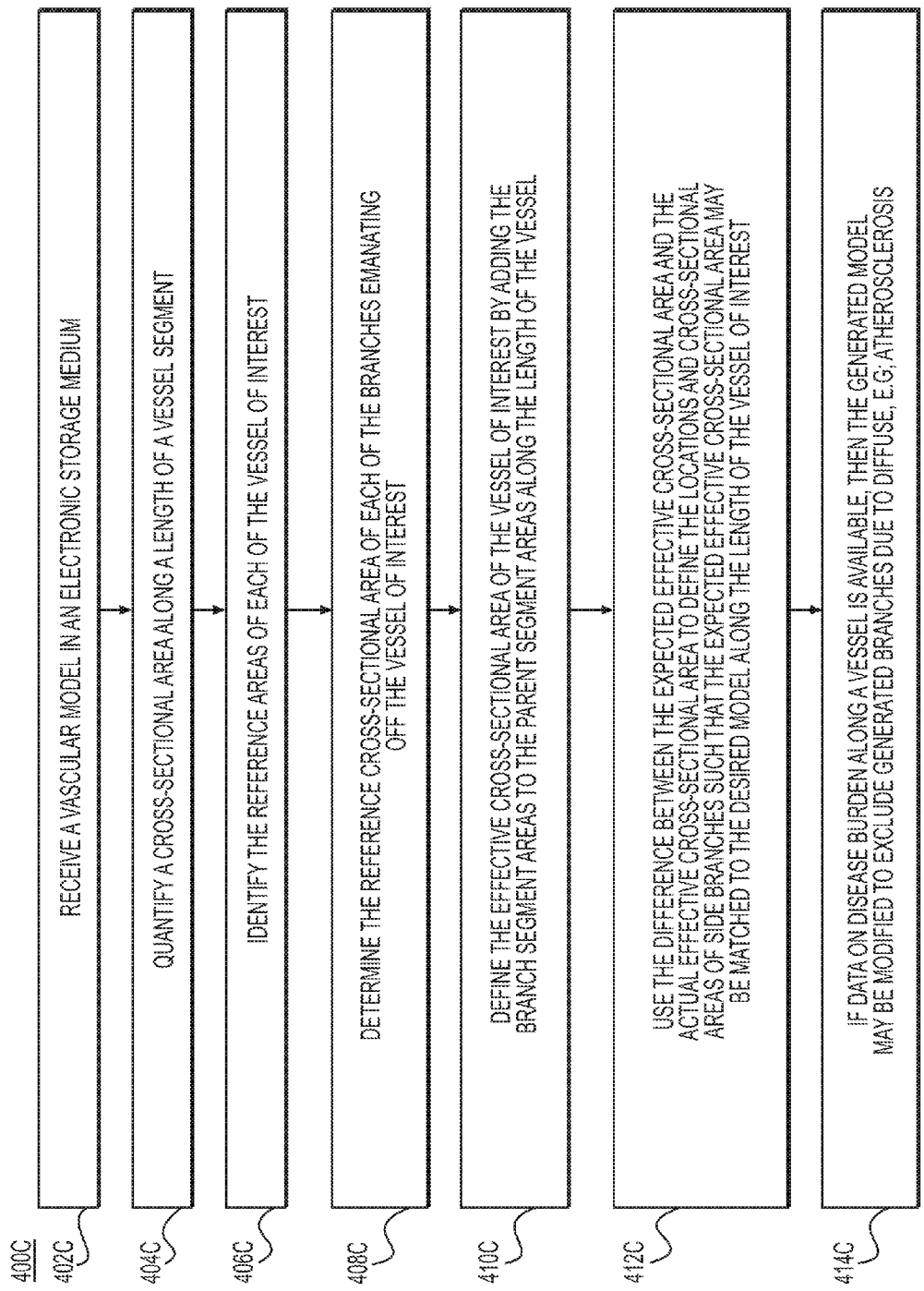

FIG. 4C depicts a method 400C of determining the values and characteristics of unresolved and/or unmodeled segments of a vascular model, using a cross-sectional area of a vessel.

Step 402C may include receiving a vascular model (e.g., a coronary vascular model) in an electronic storage medium (e.g., as in step 302). In some embodiments, the vascular model received may be of a vascular region other than a coronary region. In other embodiments, step 402C may include, like step 202, receiving one or more patient-specific anatomical models representing a vasculature of a patient in one or more physiological or temporal states (e.g., future, past, prospective, etc.).

Step 404C may include quantifying a cross-sectional area along a length of a vessel segment. This may be performed by defining an orthogonal plane at a given location along the centerline and slicing the patient-specific anatomic model to extract a cross-sectional area at one or more locations along the centerline. Alternatively or additionally, step 404C may include calculating the diameter of the largest inscribed sphere that can be contained within the model along the length of the vessel. In either case, the resultant data on cross-sectional area along the length of the vessel may include the effect of branch arteries and stenoses. Branch arteries may typically cause the cross-sectional area to rise abruptly, for example. In a stenosis, the cross-sectional area may diminish abruptly in the case of a focal lesion or more gradually in the case of a long lesion.

Step 406C may include identifying the reference area along the vessel of interest. A smooth function may be fit to the data on cross-sectional area along the length of the vessel.

Step 408C may include determining the reference cross-sectional area of each of the branches emanating off the vessel of interest. Step 408C may be performed using the method described in step 404C for the vessel of interest or by sampling the cross-sectional area of the branch in a non-diseased segment at a location downstream of the location where the branch vessel emanates from the parent vessel.

Step 410C may include defining the effective cross-sectional area of the vessel of interest by adding the branch segment areas to the parent segment areas along the length of a vessel. Unlike the monotonically decreasing reference cross-sectional area along the length of the parent vessel, the effective cross-sectional area (which includes the area of the branch vessels) should be preserved or actually increase continuously along the length of the vessel. However, due to image quality and/or image resolution limitations, this effective cross-sectional area function may generally decrease at some locations along the length of the vessel.

Step 412C may include using the difference between the expected effective cross-sectional area (i.e. non-decreasing down a vessel) and the actual effective cross-sectional area to define the locations and cross-sectional areas of side branches such that the expected effective cross-sectional area may be matched to the desired model (e.g. constant, slightly increasing, etc.) along the length of the vessel of interest. For example, one or more branch vessels with a net cross-sectional area matching that of the difference in expected and actual effective areas could be added at locations to ensure smooth variations in actual area. In another embodiment, given a target effective cross sectional area, divergence from the target difference by more than some threshold value could indicate the need to add branches.

In some embodiments, if data on disease burden along the vessel is available, e.g., by detecting plaque in the CT data, then step 414C may include modifying the generated model to exclude generated branches due to, e.g., diffuse atherosclerosis. This diffuse disease may also be estimated by computing the ratio of the coronary arterial volume to the myocardial mass or volume or the ratio of the arterial lumen volume to the summed length (as in, e.g., Huo Y., Wischgoll T., Choy J S., Sola S., Navia J L., Teague S D., et al. CT-based diagnosis of diffuse coronary artery disease on the basis of scaling power laws. Radiology 2013; 268:694-701).

Figure 4D:
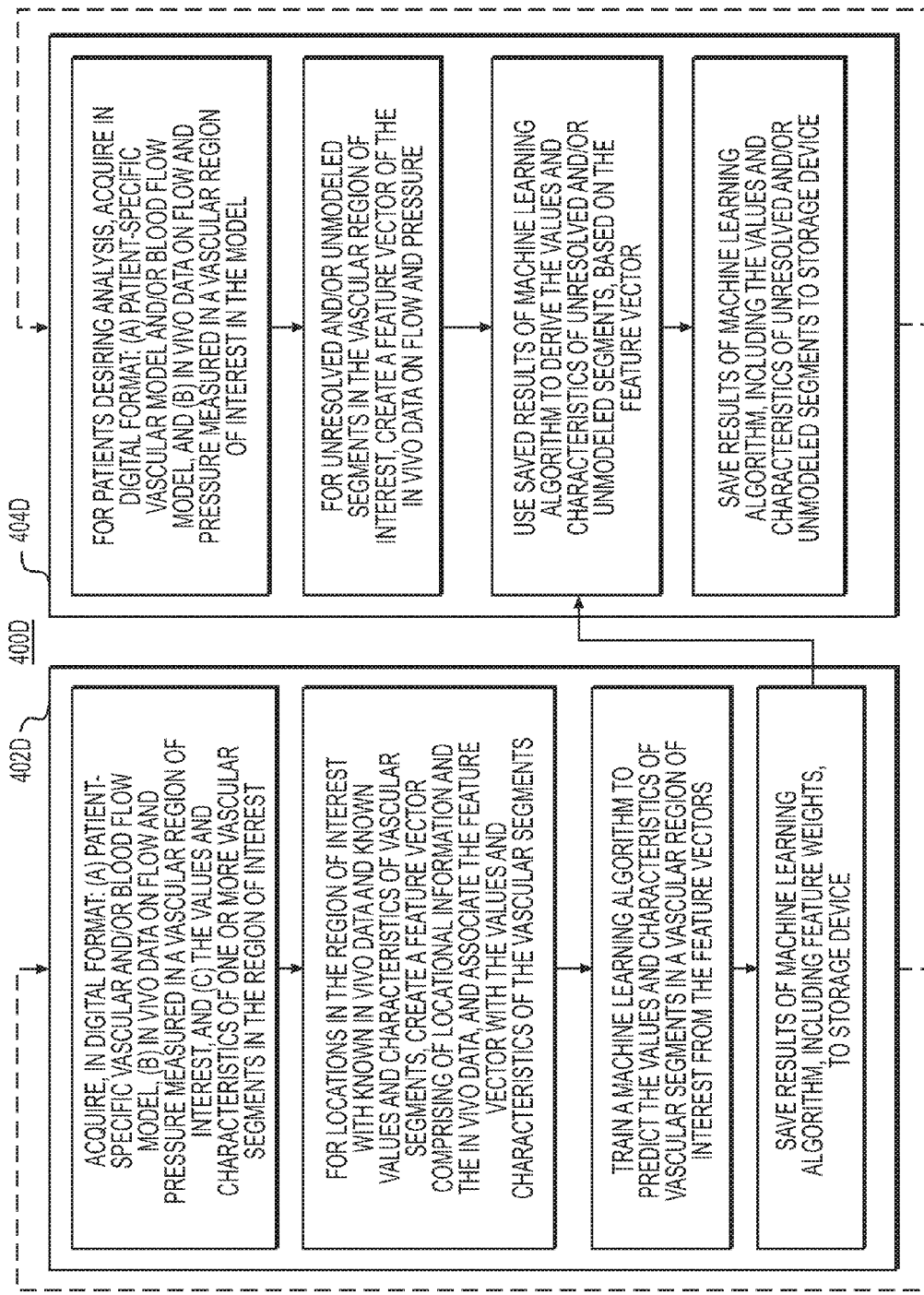

FIG. 4D depicts a method 400D of determining the values and characteristics of unresolved and/or unmodeled segments of a vascular model using a machine learning algorithm. The method 400D of FIG. 4D may be performed by server systems 106, based on information received from physicians 102 and/or third party providers 104 over electronic network 100.

In one embodiment, the method 400 of FIG. 4D may include a training method 402D, for training one or more machine learning algorithms based on in vivo data on blood flow and pressure in a vascular region of interest from numerous patients and measured, estimated, and/or simulated values and characteristics of vascular segments in the vascular region of interest, and a production method 404D for using the machine learning algorithm results to predict the values and characteristics of unresolved and/or unmodeled vascular segments in a vascular region of interest.

In one embodiment, training method 402D may involve acquiring, for each of a plurality of individuals, e.g., in digital format: (a) a patient-specific vascular and/or a blood flow model, (b) a measured or derived in vivo data on blood flow and pressure for one or more points of a vascular region of interest in the received model, and (c) the values and characteristics of the vascular segments in the vascular region of interest.

In some embodiments, the in vivo data may be obtained from a source of reference data (e.g., high resolution imaging from cadavers, intravascular imaging such as optical coherence tomography (OCT), intravascular ultrasound (IVUS), angiography, etc.). In other embodiments, the data on blood flow and pressure may be in vitro.

Training method 402D may then involve, for one or more points in each patient's model, creating a feature vector comprising of the locational information at one or more points of the vascular and/or blood flow model and the in vivo data, and associating the feature vector with the values and characteristics of the vascular segments in the vascular region of interest.

Training method 402D may then save the results of the machine learning algorithm, including feature weights, in a storage device of server systems 106. The stored feature weights may define the extent to which patient-specific parameters and/or anatomical location are predictive of blood flow and/or blood supply demand characteristics.

In one embodiment, the production method 404D may involve estimating the values and characteristics of unresolved and/or unmodeled vascular segments in a vascular region of interest for a particular patient, based on results of executing training method 402D. In one embodiment, production method 404D may include acquiring, e.g. in digital format: (a) a patient-specific vascular and/or blood flow model of a patient seeking analysis (e.g., as in step 302 or step 304 of FIG. 3, respectively), and (b) measured or derived in vivo data on blood flow and pressure in a vascular of interest in the model. For multiple points in the vascular region of interest in the patient's vascular and/or blood flow model, production method 404D may involve creating a feature vector comprising of the locational information and the in vivo data on blood flow and pressure, as used in training method 402D. Production method 404D may then use saved results of the machine learning algorithm to produce estimates of the values and characteristics of unresolved and/or unmodeled vascular segments in the vascular region of interest in the patient-specific vascular and/or blood flow model of the patient. Finally, production method 404D may include saving the results of the machine learning algorithm, including the values and characteristics of unresolved and/or unmodeled segments to a storage device of server systems 106.

In some embodiments, the values and characteristics of unresolved and/or unmodeled vascular segments may include the quantity and size of branches at each location in the vascular model. If the unresolved and/or unmodeled vascular segments did not exist in the acquired patient-specific vascular and/or blood flow model of the patient, method 404D may include modifying the model to include the previously unresolved and/or unmodeled vascular segments.

In some embodiments, the machine learning techniques used in method 400D may be used to estimate the effect on the fluid dynamics (e.g. errors in pressure gradients or flow rate) resulting from un-modeled branches in the modeled computational domain. The original model may then be further corrected, either through directly modifying the mathematical formulation of the blood flow model itself or as a post-processing step operating on the results from the original blood flow model.

In some embodiments, the machine learning techniques may include using one or more of: a support vector machine (SVM), a multi-layer perceptron (MLP), a multivariate regression (MVR), deep learning, random forests, k-nearest neighbors, Bayes networks, or a weighted linear or logistic regression.

FIG. 5 depicts methods 500A and 500B of modifying a vascular and/or blood flow model with information on unresolved and/or unmodeled segments, according to an exemplary embodiment of the present disclosure. Moreover, methods 500A and/or 500B may be used to perform step 208 of method 200 or step 308 of method 300.

For example, method 500A may be performed to modify a vascular and/or blood flow model by augmenting the model with additional branches.

Step 502A may include receiving information on the quantity, location, and/or dimensions of unresolved side branches. The information may be received by performing step 206 of method 200 or step 306 of method 300, for example, by using one or more of methods 400A-D.

Step 504A may include augmenting the blood flow model and/or vascular anatomical model with additional branches, according to the received information. The received information may include information on the quantity and dimensions of unresolved side branches. In some embodiments, the augmentation may occur on the computational domain of the original 3D, 1D, 0D or machine learning-based blood flow model with additional branches. In an embodiment where the original model is in 3D, the additional branches may be represented with actual 3D extensions of the original geometry or with 1D, 0D or machine learning-based models coupled to the original domain.

Step 506A may include readjusting the boundary conditions to maintain the flow rates proximal to the segments with added branches. In some embodiments, the boundary conditions may be those located at each of the outflow boundaries, original and new. The boundary conditions may be re-adjusted to maintain the same flowrates proximal to the segments with added branches, thereby maintaining consistency of the solution in the larger arteries of interest with that of the original model.

Additionally or alternately, method 500B may performed to modify a vascular and/or blood flow model using a permeability function.

Step 502B may include receiving information on the quantity, location, and/or dimensions of unresolved side branches. The information may be received by performing step 206 of method 200 or step 306 of method 300, for example, by using one or more of methods 400A-D. In some embodiments, the received information may include the estimated locations and dimensions of the unresolved branches.

Step 504B may include defining a permeability function whereby flow may be extracted along the length of the vessel in order to reduce the pressure gradient. In some embodiments, the received information from step 502B (e.g., the estimated locations and dimensions of the unresolved branches) may be used to define the permeability function. The outflow function may be defined as a function of length along the vessel. Such outflow functions were originally defined in the early 1970s to enable solutions of the non-linear one-dimensional wave propagation models of blood flow (see e.g. M. Anliker, L. Rockwell, and E. Ogden, "Nonlinear Analysis of Flow Pulses and Shock Waves in Arteries," ZAMP, vol. 22, pp. 217-246, 1971; Hughes, T. J. R. and J. Lubliner. On the one-dimensional theory of blood flow in the larger vessels. Math. Biosci. 18:161-170, 1973.). However, this method has not been previously described for accounting for missing branches.

Step 506B may include readjusting the boundary conditions so that they are consistent with the defined permeability function. In some embodiments, the boundary conditions may be those located at each of the outflow boundaries, original and new. The boundary conditions may be re-adjusted to maintain the same flowrates proximal to the segments with added branches, thereby maintaining consistency of the solution in the larger arteries of interest with that of the original model.

In some embodiments for modifying a vascular and/or blood flow model with information on unresolved and/or unmodeled segments (e.g. for methods 500A-B), the added branches may serve as outlets that divert flow from the parent vessel, thereby reducing the pressure gradient. In an alternate embodiment, the added branches may also represent the effect of unseen source branches that contribute flow to a main vessel. A specific application may be the modeling of the collateral circulation in the coronary arteries, where a main vessel with a lesion may be directly observed and reconstructed from image data but collateral channels may not be. A patient may have a heavily stenosed region in a main coronary vessel but also well-developed collateral pathways that divert flow around the lesion and adequately perfuse the downstream myocardium. In this case, the actual pressure gradient across the stenosis may be less severe than predicted using a model that fails to account for the collaterals. In this embodiment, the process of detection and inclusion of additional branches is as described previously in the present disclosure; however, added branches in the model may be treated as sources that contribute flow to the parent vessel in addition to sinks that divert flow from the parent vessel.

The methods described in the various embodiments of the present disclosure may also be applied to models of any part of the cardiovascular system where medical imaging techniques are used to image the major blood vessels and where modeling the effects of branches just beyond the limits of image resolution may be desirable. For example, the methods described in the present disclosure may apply to the simulation of blood flow in the brain, whereby small side branches may be commonly found along the length of the larger cerebral arteries. Inclusion of these small branches may aid in simulations of brain perfusion, for example. Other examples may include the hepatic circulation, the peripheral vasculature of the upper and lower extremities, the renal vasculature, and the mesenteric vasculature where numerous side branches supply blood to the small and large intestines.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A computer-implemented method of identifying and modeling unresolved vessels, and effects thereof, in image-based patient-specific hemodynamic models, the method comprising:

receiving, in an electronic storage medium, one or more patient-specific anatomical models representing at least a vessel of a patient;

determining, using a processor, values and characteristics of one or more patient-specific morphometric features in the one or more patient-specific anatomical models;

determining values or characteristics of one or more unresolved or unmodeled vessels in the one or more patient-specific anatomical models;

modifying the one or more patient-specific anatomical models using the determined patient-specific morphometric features and the determined values or characteristics of the one or more unresolved or unmodeled vessels; and outputting, one or more of, a modified patient-specific anatomical model or a patient-specific morphometric feature to an electronic storage medium or display.

2. The computer-implemented method of claim 1, further comprising:

determining a blood flow characteristic using the one or more modified patient-specific anatomical models; and outputting one or more of the determined blood flow characteristic or a hemodynamic simulation using the determined blood flow characteristic to an electronic storage medium or display.

3. The computer-implemented method of claim 1, wherein the one or more patient-specific anatomical models includes patient-specific anatomical models representing at least a vessel of a patient in one or more physiological states, the physiological states including, one or more of:

a normal state;
a resting state;
an exercise-induced or hyperemic state;
a drug-induced hyperemic state;
a drug-induced resting state;
a positional state;
a post prandial state; or
a gravitational state.

4. The computer-implemented method of claim 1, wherein the values and characteristics of morphometric features include one or more of:

data related to blood flow and pressure in the vessel of the patient-specific anatomical model;

a presence or a location of unresolved or unmodeled vascular branches in the vascular model;

a quantity of unresolved or unmodeled vascular branches at each location in the vascular model;

a length, diameter, or size of the unresolved or unmodeled vascular branches at each location in the vascular model; and an effect of the unresolved or unmodeled vascular segments on the fluid dynamics of blood flow.

5. The computer-implemented method of claim 1, wherein determining, using a processor, the values and characteristics of one or more patient-specific morphometric features in the one or more patient-specific anatomical models includes:

measuring or deriving, from the one or more patient-specific anatomical models, a length, a diameter, or both, of a modeled or resolved vascular segment;

receiving reference values for a length-to-diameter ratio of a vessel in a reference vascular region, the vessel corresponding with the modeled or resolved vascular segment in the one or more patient-specific anatomical models; and determining the values and characteristics of any one or more unmodeled or unresolved vascular segments branching from the modeled or resolved vascular segment, using the length, diameter, or both, of a modeled or resolved vascular segment from the one or more patient-specific anatomical models, and the reference values for the length-to-diameter ratio of the vessel.

6. The computer-implemented method of claim 1, wherein determining, using a processor, the values and characteristics of one or more patient-specific morphometric features in the one or more patient-specific anatomical models includes:

identifying a vessel of interest in a patient-specific anatomical model;

determining one or more of a vascular volume or a vascular resistance of the vessel of interest;

appending or substituting a synthesized vascular tree to the vessel of interest;

computing one or more of an expected total vascular volume or an expected total vascular resistance of the substituted synthesized vascular tree or the vessel of interest and the appended synthesized vascular tree; and determining the values and characteristics of unresolved or unmodeled vascular segments that branch from the vessel of interest, using the difference between the vascular volume or vascular resistance of the vessel of interest and an expected total vascular volume or expected total vascular resistance.

7. The computer-implemented method of claim 1, wherein determining, using a processor, the values and characteristics of one or more patient-specific morphometric features in the one or more patient-specific anatomical models includes:

measuring or obtaining a cross-sectional area along a length of a vessel of interest in a patient-specific anatomical model;

identifying a reference vessel corresponding to the vessel of interest, the reference vessel belonging to the same or similar vascular region as the vessel of interest;

identifying one or more vascular segments branching from the reference vessel, the one or more vascular segments branching from the reference vessel being unmodeled or unresolved in the patient-specific anatomical model;

receiving a cross-sectional area of the one or more vascular segments branching from the reference vessel;

determining an effective cross-sectional area of the vessel of interest by adding the cross-sectional area of the one or more vascular segments branching from the reference vessel and a cross-sectional area along the length of a vessel of interest; and determining a value and a characteristic of unmodeled or unresolved vascular segments branching from the vessel of interest in the patient-specific anatomical model, using the difference between the determined effective cross-sectional area of the vessel of interest and the measured or obtained cross-sectional area of the vessel of interest.

8. The computer-implemented method of claim 1, wherein the patient-specific anatomical model includes at least a vessel from, one or more of, a coronary vascular model;
a cerebral vascular model;
a peripheral vascular model;
a hepatic vascular model;
a renal vascular model;
a visceral vascular model; or
any vascular model with one or more unmodeled or unresolved vessels.

9. The computer-implemented method of claim 1, wherein modifying the patient-specific anatomical model using the determined patient-specific morphometric features includes:
augmenting the patient-specific anatomical model with additional vascular segments, using the patient-specific morphometric features; and
readjusting one or more boundary conditions of the patient-specific anatomical model to maintain the flow rates proximal to vessels with added vascular segments.

10. The computer-implemented method of claim 1, wherein modifying the patient-specific anatomical model using the determined patient-specific morphometric features includes:
truncating the patient-specific anatomical model to exclude, at least, the unresolved vascular segments, using the patient-specific morphometric features; and
readjusting one or more boundary conditions of the truncated patient-specific anatomical model to maintain a flow rate proximal to vessels with the removed vascular segments.

11. The computer-implemented method of claim 1, wherein modifying the patient-specific anatomical model using the determined patient-specific morphometric features includes:
defining a permeability function whereby flow may be extracted along a length of the vessel in order to reduce a pressure gradient; and
readjusting one or more boundary conditions of the patient-specific anatomical model so that they are consistent with the permeability function.

12. The computer-implemented method of claim 1, wherein modifying the patient-specific anatomical model using the determined patient-specific morphometric features includes:
modifying the patient-specific anatomical model to exclude any one or more vascular segments branching from the vessel of interest due to a disease burden.

13. The computer-implemented method of claim 1, further comprising:
receiving a patient-specific blood flow model representing one or more blood flow characteristics of the vessel of the patient-specific anatomical model; and
modifying the patient-specific blood flow model based on the determined patient-specific morphometric features; and
outputting, one or more of, the modified patient-specific blood flow model or a patient-specific morphometric feature to an electronic storage medium or display.

14. A system for identifying and modeling unresolved vessels, and effects thereof, in image-based patient-specific hemodynamic models, the system comprising:
a data storage device storing instructions for identifying and modeling unresolved vessels, and the effects thereof, in image-based patient-specific hemodynamic models; and
a processor configured to execute the instructions to perform a method comprising:
receiving, in an electronic storage medium, one or more patient-specific anatomical models representing at least a vessel of a patient;
determining, using a processor, values and characteristics of one or more patient-specific morphometric features in the one or more patient-specific anatomical models;
determining values or characteristics of one or more unresolved or unmodeled vessels in the one or more patient-specific anatomical models;
modifying the patient-specific anatomical model using the determined patient-specific morphometric features and the determined values or characteristics of the one or more unresolved or unmodeled vessels; and
outputting, one or more of, a modified patient-specific anatomical model or a patient-specific morphometric feature to an electronic storage medium or display.

15. The system of claim 14, further comprising:
determining a blood flow characteristic using the one or more modified patient-specific anatomical models; and
outputting one or more of the determined blood flow characteristic or a hemodynamic simulation using the determined blood flow characteristic to an electronic storage medium or display.

16. The system of claim 14, wherein the values and characteristics of morphometric features include one or more of:
data related to blood flow and pressure in at least a vessel of the patient-specific anatomical model;
a presence or a location of unresolved or unmodeled vascular branches in the vascular model;
a quantity of unresolved or unmodeled vascular branches at each location in the vascular model; and
a length, diameter, or size of the unresolved or unmodeled vascular branches at each location in the vascular model; and
an effect of the unresolved or unmodeled vascular segments on the fluid dynamics of blood flow.

17. The system of claim 14, wherein determining, using a processor, the values and characteristics of one or more patient-specific morphometric features in the one or more patient-specific anatomical models includes:
measuring or deriving, from the one or more patient-specific anatomical models, a length, a diameter, or both, of a modeled or resolved vascular segment;
receiving reference values for a length-to-diameter ratio of a vessel in a reference vascular region, the vessel corresponding with the modeled or resolved vascular segment in the one or more patient-specific anatomical models; and
determining the values and characteristics of any one or more unmodeled or unresolved vascular segments branching from the modeled or resolved vascular segment, using the length, diameter, or both, of a modeled or resolved vascular segment from the one or more patient-specific anatomical models, and the reference values for the length-to-diameter ratio of the vessel.

18. The system of claim 14, wherein determining, using a processor, the values and characteristics of one or more patient-specific morphometric features in the one or more patient-specific anatomical models includes:
identifying a vessel of interest in a patient-specific anatomical model;
determining one or more of a vascular volume or a vascular resistance of the vessel of interest;

appending or substituting a synthesized vascular tree to the vessel of interest;

computing one or more of an expected total vascular volume or an expected total vascular resistance of the substituted synthesized vascular tree or the vessel of interest and the appended synthesized vascular tree; and determining the values and characteristics of unresolved or unmodeled vascular segments that branch from the vessel of interest, using a difference between the vascular volume or vascular resistance of the vessel of interest and the expected total vascular volume or expected total vascular resistance.

19. The system of claim 14, wherein determining, using a processor, the values and characteristics of one or more patient-specific morphometric features in the one or more patient-specific anatomical models includes:

measuring or obtaining a cross-sectional area along a length of a vessel of interest in a patient-specific anatomical model;

identifying a reference vessel corresponding to the vessel of interest, the reference vessel belonging to the same or similar vascular region as the vessel of interest;

identifying one or more vascular segments branching from the reference vessel, the one or more vascular segments branching from the reference vessel being unmodeled or unresolved in the patient-specific anatomical model;

receiving a cross-sectional area of the one or more vascular segments branching from the reference vessel;

determining an effective cross-sectional area of the vessel of interest by adding the cross-sectional area of the one or more vascular segments branching from the reference vessel and a cross-sectional area along the length of a vessel of interest; and determining a value and a characteristic of unmodeled or unresolved vascular segments branching from the vessel of interest in the patient-specific anatomical model, using the difference between the determined effective cross-sectional area of the vessel of interest and the measured or obtained cross-sectional area of the vessel of interest.

20. A non-transitory computer-readable medium storing instructions that, when executed by a computer, cause the computer to perform a method for identifying and modeling unresolved vessels, and effects thereof, in image-based patient-specific hemodynamic models, the method including:

receiving, in an electronic storage medium, one or more patient-specific anatomical models representing at least a vessel of a patient;

determining, using a processor, values and characteristics of one or more patient-specific morphometric features in the one or more patient-specific anatomical models;

determining values or characteristics of one or more unresolved or unmodeled vessels in the one or more patient-specific anatomical models;

modifying the patient-specific anatomical model using the determined patient-specific morphometric features and the determined values or characteristics of the one or more unresolved or unmodeled vessels; and outputting, one or more of, a modified patient-specific anatomical model or a patient-specific morphometric feature to an electronic storage medium or display.

* * * * *